United States Patent [19]
Cronk et al.

[11] Patent Number: 5,706,800
[45] Date of Patent: Jan. 13, 1998

[54] MEDICATED NASAL DILATOR

[76] Inventors: Peter J. Cronk; Kristen Cronk, both of 919 McElwee Rd., Moorestown, N.J. 08057

[21] Appl. No.: 791,760

[22] Filed: Jan. 29, 1997

[51] Int. Cl.$^6$ .............................. A61F 5/08; A61M 15/00; A61M 16/00; A62B 7/00

[52] U.S. Cl. .................. 128/200.24; 128/207.14; 128/204.13; 606/199; 606/204.45

[58] Field of Search .............. 128/200.24, 207.18, 128/912, 848, 204.13, DIG. 26; 606/199, 204.45; 602/74, 41, 47, 54, 55, 56, 57–59, 902

[56] References Cited

U.S. PATENT DOCUMENTS

| | | | |
|---|---|---|---|
| D. 310,565 | 9/1990 | Petruson . | |
| 3,710,799 | 1/1973 | Caballero | 128/342 |
| 5,533,503 | 7/1996 | Doubek et al. | 128/200.24 |
| 5,546,929 | 8/1996 | Muchin | 128/200.24 |
| 5,549,103 | 8/1996 | Johnson | 128/200.24 |
| 5,611,333 | 3/1997 | Johnson | 128/200.24 |

OTHER PUBLICATIONS

CNS Inc., *Breathe Right® Instructions*, 1995.
B4–U–Buy™ FYI, http://www.b4–u–buy.com/snorers.html, *New Device Offers Relief for Snorers.*
Sigma Online Catalog, *Nozovent.*
Abstract entitled: Two New Ways for Nasal Administration of Drugs with the Nasal Dilator Nozovent, B. Petruson, Univ. of Götenborg, Sweden.

*Primary Examiner*—Kimberly L. Asher
*Attorney, Agent, or Firm*—Duane, Morris & Heckscher LLP

[57] ABSTRACT

Nasal dilators and methods for improving the breathing of individuals are provided. The dilator includes an elongated substrate having top and bottom surfaces and a pressure-sensitive adhesive disposed on the bottom surface. A resilient member is bonded to the substrate to provide a gentle expanding force to the nasal wall tissue when the dilator is adhesively attached to the nose. This invention further includes an aromatic medication or transdermal medication disposed on the dilator to further improve breathing. Ideal aromatic medications include camphor and menthol. Reinforcing scrims, layers and thermoplastics melt-bonding procedures are also provided for improving properties and minimizing costs.

25 Claims, 2 Drawing Sheets

MEDICATED NASAL DILATOR

FIELD OF THE INVENTION

This invention relates to dilators for easing the breathing of patients, and more particularly to medicated nasal dilators for preventing outer wall tissue of nasal passages from drawing in during breathing while providing medication to the patient.

BACKGROUND OF THE INVENTION

Nasal dilators have been suggested for aiding breathing through the nose. There have been traditionally two types of dilators which have been effective in humans. One type uses small rings or cages connected to a resilient structure. The rings are inserted into each nasal passage while the resilient structure spreads to provide unobstructed breathing. These dilators have been criticized because they are often uncomfortable to wear. Since the cages or rings are inserted into contact with sensitive nasal tissue, they have been known to cause irritation and itching. Such devices are disclosed in U.S. Pat. No. 3,710,799 to Caballero and the NOZOVENT dilator disclosed in Petruson D310,565.

More recently, advancements have been made in nasal dilators which attach to the outer wall tissue of the nose and aide in preventing the inner nasal tissue from drawing in during breathing. Such dilators include a flexible strip of material adhesively attached to a substrate. The dilator is fastened to the nose and the resilient material acts to keep the left and right nasal passages from drawing in or collapsing during inhalation. This usually occurs due to a malformation, such as a deviated septum or due to swelling during allergic reactions and the like. Examples of nasal dilators which are adhesively attached to the outer skin of a human nose are disclosed in Doubek et al., U.S. Pat. No. 5,533,503 and Muchin, U.S. Pat. No. 5,546,929.

While conventional nasal dilators are being used by a greater number of people, there is still a need to further improve the breathing of those individuals to a greater degree than can be established by mere mechanical manipulation of their nasal tissue.

SUMMARY OF THE INVENTION

Nasal dilators and methods of easing breathing are provided by this invention. The first group of preferred dilators include an elongated substrate having a pair longitudinal sides, a pair of transverse ends and top and bottom surfaces. Disposed on the bottom surface of the substrate is a pressure sensitive adhesive. The substrate also includes a resilient member bonded to its surface to provide a gentle expanding force to a nasal wall tissue when the dilator is adhesively attached to a nose. In an important improvement over the prior art, an aromatic medication is disposed on a portion of the dilator so that it can be inhaled through the nose of the wearer during breathing.

This invention combines the spring action of adhesively applied nasal dilators with inhaleable aromatics. Such an accommodation has the potential to produce synergistic benefits for patients who have not been entirely satisfied by either non-medicated dilators, or over-the-counter decongestant medication, some of which can cause drowsiness.

In another embodiment of this invention, a method of substantially preventing the wall tissue of a nose from drawing in during breathing is provided. The method includes providing a nasal dilator including a substrate having disposed thereon a pressure sensitive adhesive layer on a first surface and a resilient member bonded to a second surface. Impregnated into the substrate is an aromatic medication for helping the patient breathe easier. The method further includes applying the pressure sensitive adhesive layer across a nose whereby the resilient member provides a gentle expanding force to the nasal wall tissue while the aromatic medication is being inhaled.

Further embodiments of this invention include transdermal medications and resilient scrims or sheet layers bonded to the substrate for minimizing the expense of continuous processing of the dilators of this invention.

BRIEF DESCRIPTION OF THE DRAWINGS

The accompanying drawings illustrate preferred embodiments of the invention as well as other information pertinent to the disclosure, in which.

DETAILED DESCRIPTION OF THE INVENTION

This invention provides nasal dilators and methods for substantially preventing a nasal wall tissue of a nose from drawing in during breathing. As used herein, the term "aromatic" medication refers to substances and compounds which can be consumed by inhaling through the nose, such as a medicated vapor or gas. Such substances should have some efficacy in helping patients breathe easier or better.

Figure 1:
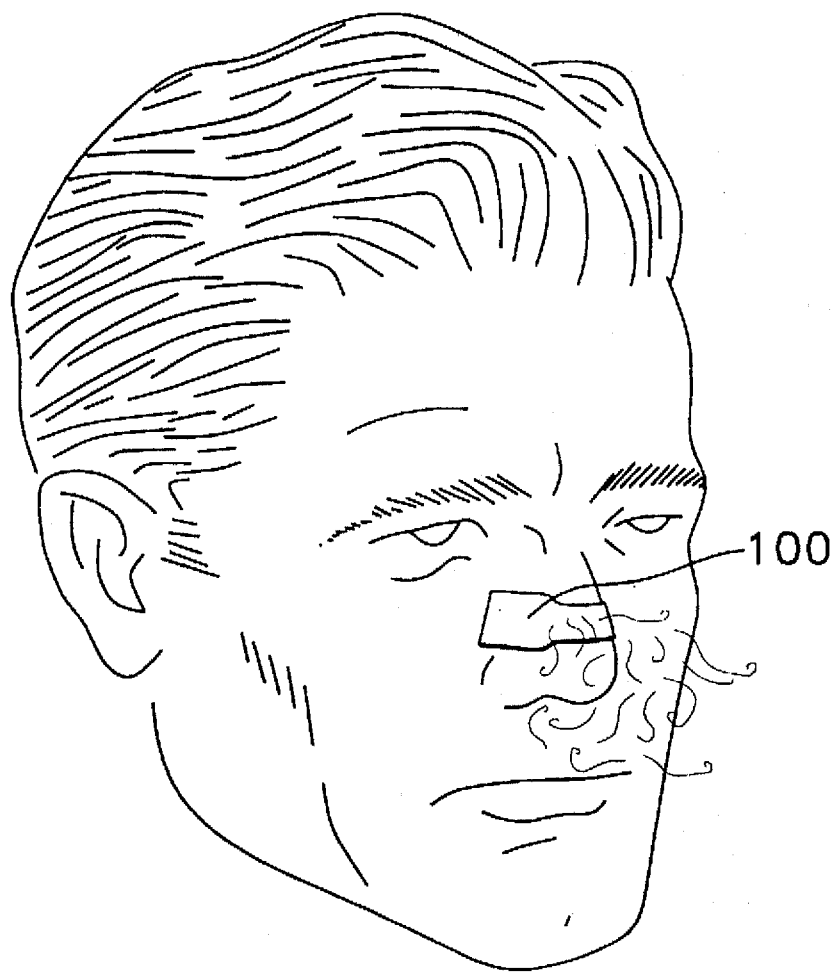
FIG. 1: is a partial front perspective view of a man wearing the preferred nasal dilator of this invention.
Figure 2:
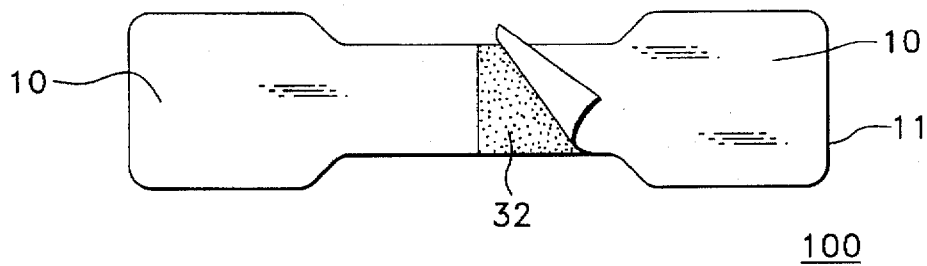
FIG. 2: is a top planar view the nasal dilator of this invention with a partial peel back view of the adhesive layer.
Figure 3:
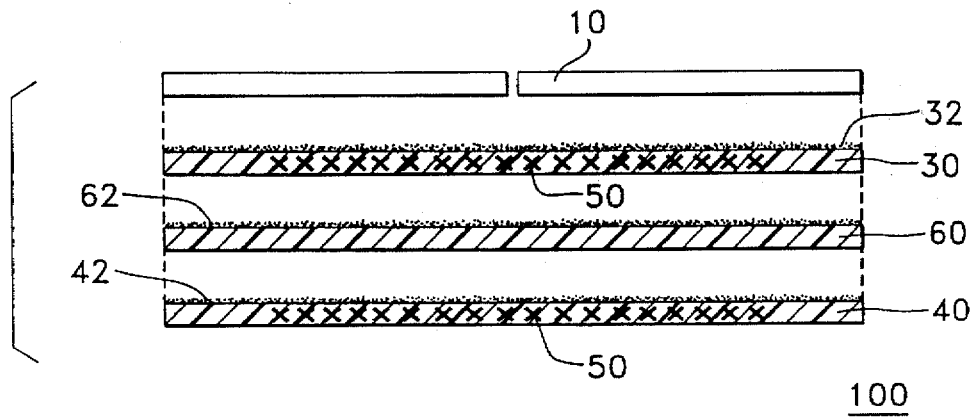
FIG. 3: is a side elevation, cross-sectional, exploded view of the nasal dilator of FIG. 2.
Figure 4:
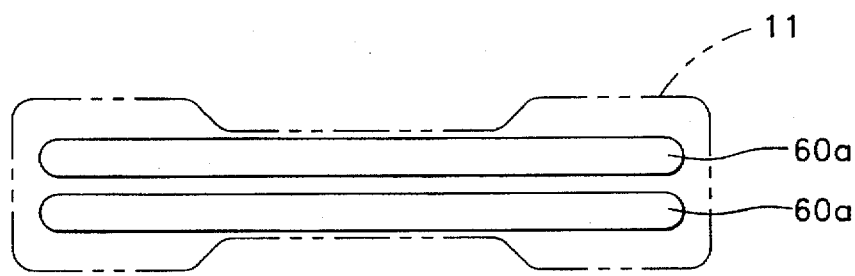
FIG. 4: is a top planar view of a preferred resilient member, including the periphery of the substrate of the nasal dilator in phantom.

With reference to the figures and in particular, FIGS. 1–3 thereof, there shown a preferred nasal dilator 100 sized to fit across the nose of the wearer so as to engage the outer wall tissue of the left and right nasal passages of the wearer. As shown in FIGS. 2–3 the nasal dilator 100 includes an elongated substrate 30 having a pair of longitudinal sides, a pair of transverse ends and top and bottom surfaces thereon. Disposed on a bottom surface of the substrate 30 is an adhesive layer 32 for permitting easy attachment to the wearer's skin. Also attached to the substrate is a resilient member 60 which provides a gentle expanding force to the nasal wall tissue when the dilator is adhesively attached to the nose. Finally, an aromatic medication 50 is disposed on a portion of the dilator so as to be inhaled through the nose of the wearer during breathing.

In further embodiments of this invention, the dilator 100 can include a backing layer 40. The backing layer 40 and resilient member 60 are desirably bonded to the substrate 30 using pressure sensitive adhesive layers 42 and 62. As shown in FIG. 3 the aromatic medication can be disposed on any surface of the dilator 100. Preferably the aromatic medication 50 is disposed on an absorbent layer portion of the dilator 100. The absorbent layer portion can be a separate absorbent layer or a portion of the elongated substrate 30 or backing layer 40. Alternatively, the aromatic medication can be disposed in one of the adhesive layers in an admixture or segregated form. Finally, a release paper strip 10 can be added over the pressure sensitive adhesive layer 32 prior to packaging the strip for sale.

The elongated substrate 30 of this invention may include any thin, flexible, breathable material for maximizing comfort. Preferably this material permits the passage of air and moisture vapor, such as perspiration. The elongated substrate can include, for example, a woven or non-woven fabric material, such as non-woven, polyester fabric. One good example is a fabric produced by DuPont E. I. de Nemours & Co., Inc. under the trademark Sontara®. Alternatively, the elongated substrate 30 can include a thermoplastic woven or non-woven fabric, such as spunbonded polyethylene or polypropylene. The substrate 30 can also be treated with the aromatic medication 50 of this invention, along with a hydrophilic or hydrophobic additive for absorbing or repelling sweat or moisture on a selective basis.

Attached to the substrate 30 on the nose skin-facing side or bottom surface of the substrate 30 is an adhesive layer 32. This adhesive layer, along with optional adhesive layers 62 and 42 can be made of a pressure sensitive biocompatible adhesive material. As used herein, "pressure-sensitive" refers to any releasable adhesive or releasable tenacious means. Adhesive compositions suitable for nasal dilators include water-based pressure-sensitive adhesives, such as acrylate adhesives, thermoplastics "hot melt" adhesives, two-sided adhesive tape, elastomer-based adhesives, and acrylic adhesives. Good examples include 3M1509 double-sided medical tape provided by 3M Inc., St. Paul, Minn. This product is a double-sided transparent polyethylene film, coated on both sides with a hypoallergenic, pressure-sensitive acrylate adhesive, supplied on a paper liner. Of course, adhesive layers 62 and 42 need not be a pressure-sensitive type at all, since once the resilient member 60 and backing layer 40 are adhered to the substrate 30, it is undesirable for these layers to separate during application or removal of the dilator from the nose.

The resilient member 60 of this invention preferably includes one or more spring strips 60a which can be die-cut from spring ribbon material. Good examples of spring ribbon material include biaxially oriented polyester that is approximately 0.01 inches thick, but polyethylene or polypropylene strips of like thickness would also provide expanding force to the dilator 100. Fiber additions to the resin of the spring strips 60a, such as, glass, graphite, carbon or boron will also improve resiliency.

Figure 5:
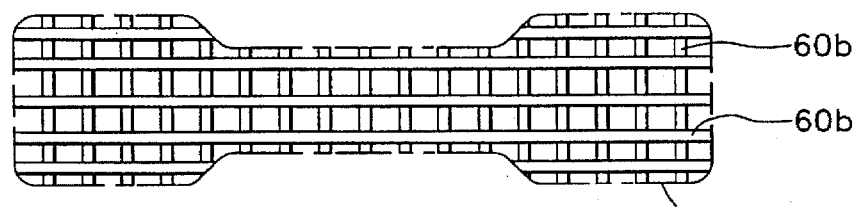
FIG. 5: is a top planar view of an alternative resilient member consisting of a reinforcing scrim also depicting the periphery of the substrate in phantom.

Alternatively, as shown in FIG. 5, a resilient layer, such as scrim 60b can be disposed within, or substantially along the perimeter 11 of the substrate 30 or outer peripheral region of the dilator 100. The resilient layer can be a woven oriented mat, fabric or material, or a non-woven mat material of fibers which are either adhesively or melt bonded together. Such fibers can include thermoplastic or thermosetting polymers. Examples include thermoplastic fibers, such as nylon, polyethylene, and polyester fibers, for example SPECTRA or COMPET fibers sold by Allied Signal Corp., Kevlar® 29, 49 or 149 aramid fibers sold by DuPont, glass, such as E-glass and S-Glass fibers, graphite fibers, carbon fibers, boron fibers, or combinations of these fibers. The resilient member, whether including spring strips 60a or a resilient scrim 60b or sheet layer (not shown) is preferably joined together in a webbing operation either by melt bonding, adhesive bonding or ultrasonic bonding. In conventional operations, a ribbon of resilient material and substrate material are adhesively joined together as they are fed into an overlapping position in a die or roller. Adhesive layers 42 and 62 are used to join the backing layer, resilient member 60 and elongated substrate 30 together prior to die-cutting to form the final periphery 11 of the dilator 100. The adhesive layers 42, 62 and 32 can be applied by spray, roll or knife, as is customary in the web-processing industry.

An important advantage of the resilient layer, such as scrim 60b or a sheet layer, as opposed to a pair of discrete spring strips 60a of this invention, is the elimination of a careful placement operation prior to die-cutting. Such an expensive step becomes unnecessary, since the resilient layer preferably conforms generally to the perimeter 11 of the final die-cut dilator. This can eliminate waste and minimize much of the expense of the webbing operation. It also provides for a more uniform spring action along most or all of the surface area of the dilator 100.

Additionally, this invention contemplates employing thermoplastic materials in the backing layer 40 and substrate 30, and alternatively, with respect to the resilient member 60 or layer. When thermoplastic materials are used, this invention enables inexpensive melt-bonding of the layers of material, with heat and pressure, to provide a composite nasal dilator structure. Melt-bonding could eliminate the need of additional adhesive layers 42 and 62 and provide a greater structural integrity to the dilator no matter what form of resilient member is employed. However, resilient scrim 60b is ideally suited for thermoplastic bonding of layers since it has pores for permitting softened thermoplastic material to bond between the fibers or filaments, further increasing the strength of the dilator 100, without requiring a lot of material.

In a further important aspect of this invention, the dilator can include an aromatic medication 50, transdermal medication, or both. Good examples of aromatic medications include camphor, eucalyptus oil, peppermint oil, menthol, methy salicylate, bornyl acetate, lavender oil, or a combination of these. Transdermal decongestants and antihistamines are also available, such as diphenhydramine and triprolidine transdermal antihistamine, available from Proctor and Gamble Co., Inc., Cincinnati, Ohio; others include ephedrine, dimethindene, epinastine, emedastine, and clonidine. These aromatic and transdermal medications can be mixed within adhesive layer 32, as in, for example, a dispersion-type transdermal patch formulation from acrylate copolymer adhesive or a lecithin gel based matrix. Alternatively, a rate controlling membrane could be used, such as Eudragit RL-100.

From the foregoing, it can be realized that this invention provides improved nasal dilators which include possibly synergistic combinations of mechanical and medicated aromatic or transdermal compositions. Also included are material processing improvements which add improved functionality and reduce the overall cost of the product. The dilators and methods of this invention are useful for helping individuals with deviated septums and athletes who desire more oxygen during a performance. Although various embodiments have been illustrated, this is for the purpose of describing, but not limiting the invention. Various modifications which will become apparent to one skilled in the art, are within the scope of this invention described in the attached claims.

We claim:

1. A nasal dilator for substantially preventing a nasal wall tissue of a nose from drawing in during breathing, comprising:

an elongated substrate having a pair of longitudinal sides, a pair of transverse ends, and top and bottom surfaces thereon;

a pressure sensitive adhesive layer disposed on said bottom surface of said substrate;

a resilient member bonded to said substrate to provide a gentle expanding force to said nasal wall tissue when said dilator is adhesively attached to said nose; and an aromatic medication disposed on a portion of said dilator, said aromatic medication being inhaled through said nose during breathing.

2. A nasal dilator of claim 1 wherein said resilient member comprises a resilient band or layer.

3. The nasal dilator of claim 1 wherein said aromatic medication comprises one or more of: camphor, eucalyptus oil, peppermint oil, menthol, methyl salicylate, bornyl acetate, lavender oil, or a combination thereof.

4. The nasal dilator of claim 1 further comprising an aromatic antihistamine or decongestant.

5. The nasal dilator of claim 1 further comprising a fibrous absorbent layer bonded to said substrate.

6. The nasal dilator of claim 5 further comprising a transdermal antihistamine or decongestant.

7. The nasal dilator of claim 6 wherein said aromatic medication is mixed within said adhesive layer.

8. A method of substantially preventing a nasal wall tissue of a nose from drawing in during breathing, comprising:

providing a nasal dilator including an elongated substrate having a pair of longitudinal sides, a pair of transverse ends and a top and bottom surface thereon, said substrate including a pressure sensitive adhesive layer disposed on a bottom surface of said substrate, a resilient member bonded to said substrate, and an aromatic medication disposed thereon;

applying said pressure sensitive adhesive layer across said nose, whereby said resilient member provides a gentle expanding force to said nasal wall tissue while said aromatic medication is inhaled through said nose.

9. The method of claim 8 wherein said aromatic medication comprises one or more of: camphor, eucalyptus oil, peppermint oil, menthol, methyl salicylate, bornyl acetate, lavender oil, or a combination thereof.

10. The method of claim 8 wherein said aromatic medication is disposed on an absorbent layer portion of said nasal dilator.

11. The method of claim 8 wherein said aromatic medication is substantially activated upon being warmed by body heat.

12. The method of claim 8 wherein said aromatic medication comprises menthol or camphor.

13. A nasal dilator for substantially preventing a nasal wall tissue of a nose from drawing in during breathing, comprising:

an elongated substrate having a pair of longitudinal sides, a pair of transverse ends, and a top and bottom surface thereon;

a pressure sensitive adhesive layer disposed on said bottom surface of said substrate;

a release paper strip applied to said pressure sensitive adhesive layer;

a resilient member bonded to said substrate to provide a gentle expanding force to said nasal wall tissue when said dilator is adhesively attached to said nose; and a transdermal medication disposed on said bottom surface for providing further breathing relief to said patient.

14. The nasal dilator of claim 13 wherein said transdermal medication comprises an antihistamine or decongestant.

15. The nasal dilator of claim 13 wherein said resilient member is disposed between said longitudinal sides of said substrate; and comprises a resilient plastic material.

16. The nasal dilator of claim 13 wherein said transdermal medication is disposed on a non-adhesive portion of the bottom surface of said substrate.

17. The nasal dilator of claim 13 further comprising an aromatic medication.

18. A nasal dilator for substantially preventing a nasal wall tissue of a nose from drawing in during breathing, comprising:

an elongated substrate having a pair of longitudinal sides, a pair of transverse ends, and top and bottom surfaces thereon, a pressure sensitive adhesive layer disposed on said bottom surface, at least one release paper strip disposed on said pressure sensitive layer, a resilient support member bonded to said substrate and an aromatic medication comprising camphor or menthol, or both, disposed thereon, said aromatic medication being inhaled through said nose.

19. A nasal dilator for substantially preventing a nasal wall tissue of a nose from drawing during breathing, comprising:

an elongated substrate having a peripheral edge, a pair of longitudinal sides, a pair of transverse ends, and top and bottom surfaces thereon;

a pressure sensitive adhesive layer disposed on said bottom surface of said substrate;

a resilient layer bonded to said substrate to provide a gentle expanding force to said nasal wall tissue when said dilator is adhesively attached to said nose wherein said resilient layer comprises fibers selected from: glass, graphite, carbon, resinous fibers, or a combination thereof.

20. The nasal dilator of claim 19 wherein said elongated substrate comprises a thermoplastic resinous layer and said resilient layer is melt bonded to said elongated substrate.

21. The nasal dilator of claim 20 further comprising an additional thermoplastic resinous layer disposed on an exposed top surface of said resilient layer.

22. The nasal dilator of claim 19, wherein said resilient layer comprises a scrim.

23. The nasal dilator of claim 22, wherein said scrim comprises a resinous binder.

24. The nasal dilator of claim 22, wherein said scrim and said elongated substrate are final cut from a common composite web material.

25. The nasal dilator of claim 19, wherein said resilient layer comprises a scrim, woven mat, a non-woven mat, or loose fibers bonded to said substrate by heat or adhesive.

* * * * *